United States Patent
Bellifemine

(10) Patent No.: US 9,474,899 B2
(45) Date of Patent: *Oct. 25, 2016

(54) PORTABLE DEVICE FOR TREATING INSECT BITES AND THE LIKE

(71) Applicant: TECNIMED S.R.L., Vedano Olona (Varese) (IT)

(72) Inventor: Francesco Bellifemine, Varese (IT)

(73) Assignee: TECNIMED S.R.L., Vedano Olona (IT)

( * ) Notice: Subject to any disclaimer, the term of this patent is extended or adjusted under 35 U.S.C. 154(b) by 313 days.

This patent is subject to a terminal disclaimer.

(21) Appl. No.: 14/263,606

(22) Filed: Apr. 28, 2014

(65) Prior Publication Data

US 2014/0316506 A1 Oct. 23, 2014

Related U.S. Application Data

(63) Continuation-in-part of application No. 12/514,521, filed as application No. PCT/IB2007/002473 on Aug. 21, 2007, now Pat. No. 8,712,555.

(30) Foreign Application Priority Data

Nov. 13, 2006 (IT) .............................. MI2006A2178

(51) Int. Cl.
*A61N 1/32* (2006.01)
*H01L 41/25* (2013.01)
*H01L 41/113* (2006.01)

(52) U.S. Cl.
CPC ................. *A61N 1/32* (2013.01); *H01L 41/113* (2013.01); *H01L 41/25* (2013.01); *Y10T 29/42* (2015.01)

(58) Field of Classification Search
CPC .......... A61N 1/05; A61N 1/32; A61N 1/326; A61N 1/0492; A61N 1/36014
USPC ........................... 607/50, 115, 145, 149, 150
See application file for complete search history.

(56) References Cited

U.S. PATENT DOCUMENTS

| | | |
|---|---|---|
| 3,758,827 A | 9/1973 | Schroder et al. |
| 3,826,952 A | 7/1974 | Iwasaki et al. |
| 3,829,737 A | 8/1974 | Johnsson |
| 4,297,609 A | 10/1981 | Hirao et al. |
| 4,315,180 A | 2/1982 | Kondo et al. |

(Continued)

FOREIGN PATENT DOCUMENTS

| | | |
|---|---|---|
| EP | 0 788 809 A | 8/1997 |
| WO | 03074939 A | 9/2003 |

*Primary Examiner* — Christopher D Koharski
*Assistant Examiner* — Roland Dinga
(74) *Attorney, Agent, or Firm* — Pearne & Gordon LLP

(57) ABSTRACT

A portable device for treating the bites or stings of insects and harmful creatures, comprising a monolithic containing body made in a single piece and defining an internal housing space, a piezoelectric element configured for producing a predetermined difference in electrical potential, and an actuating element operable by a user and associated with said piezoelectric element to impart to the piezoelectric element a predetermined state of stress/deformation; the actuating element, the piezoelectric element and the discharge area are aligned along the operating axis. The monolithic containing body presenting a bottom part developing along the operating axis below a guide and housing portion, the bottom part defining part of the internal housing space with an overall span orthogonal to the operating axis which is constantly smaller than an overall span of the internal housing space defined by the guide and housing portion.

20 Claims, 12 Drawing Sheets

(56) References Cited

U.S. PATENT DOCUMENTS

| | | |
|---|---|---|
| 4,703,160 A | 10/1987 | Narishima et al. |
| 4,741,347 A | 5/1988 | Robert et al. |
| 4,926,880 A | 5/1990 | Claude et al. |
| 4,982,743 A | 1/1991 | Pierson |
| 5,235,990 A | 8/1993 | Dempsey |
| 5,496,356 A | 3/1996 | Hudz |
| 5,800,504 A | 9/1998 | Bellifemine |
| 8,712,555 B2 * | 4/2014 | Bellifemine ............ 607/145 |
| 2003/0164662 A1 | 9/2003 | Amoros et al. |
| 2009/0222060 A1 | 9/2009 | Boyd et al. |

* cited by examiner

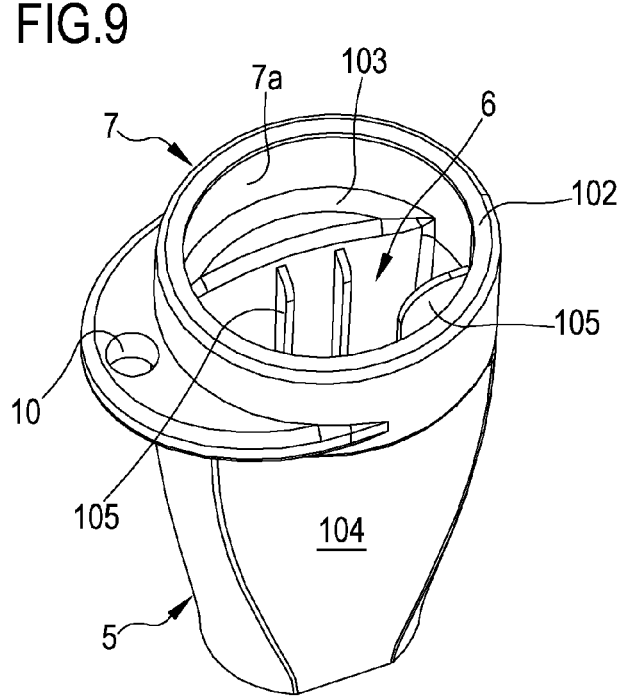
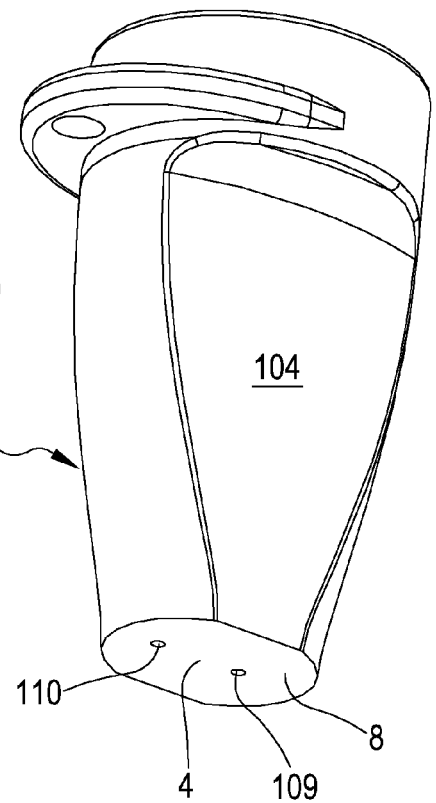
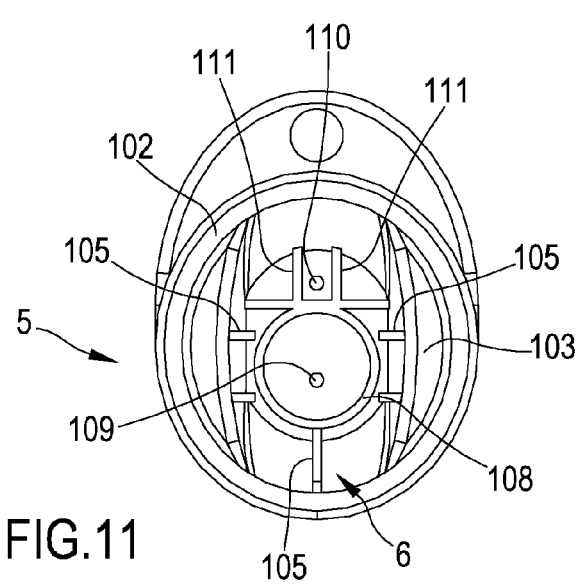

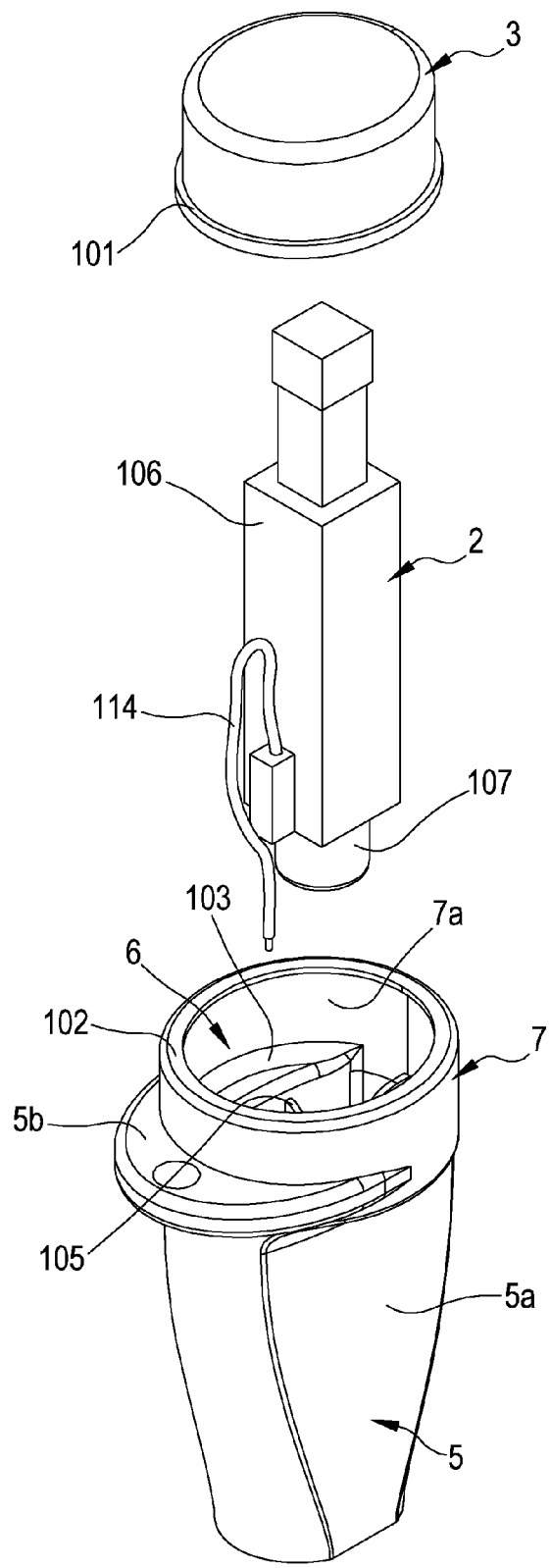

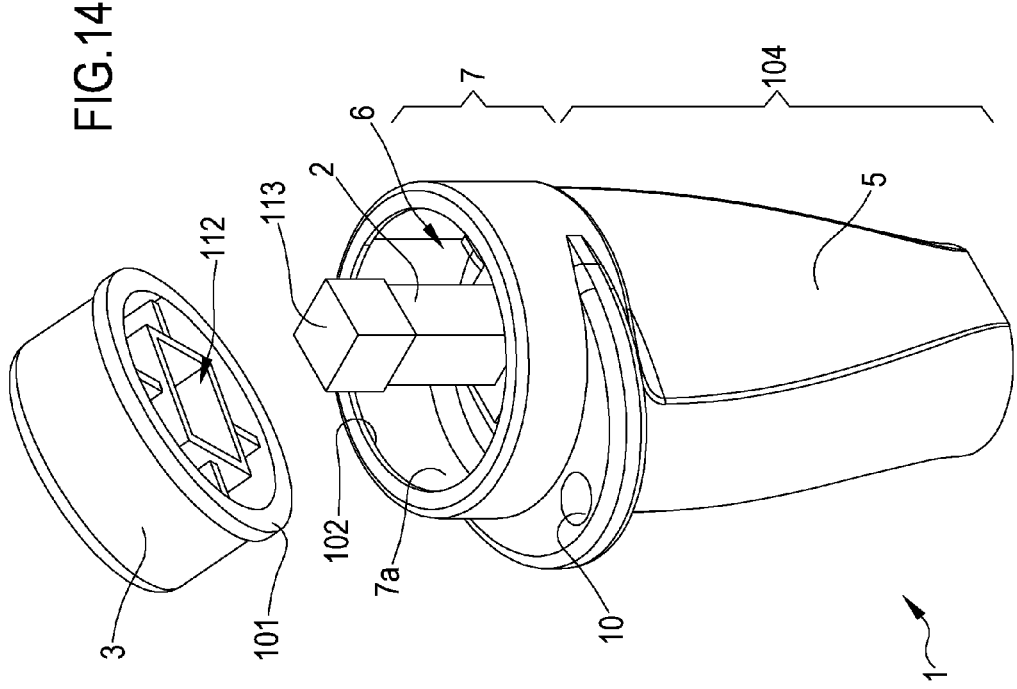
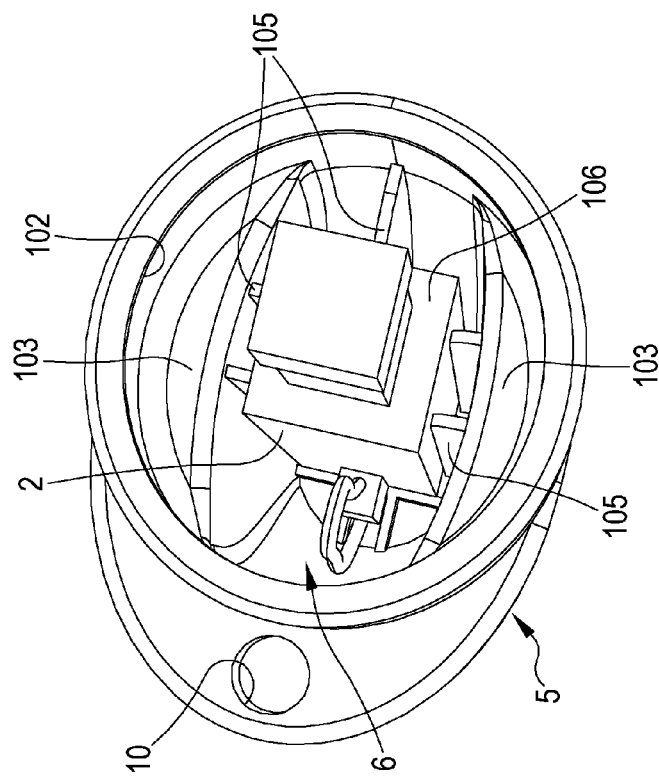

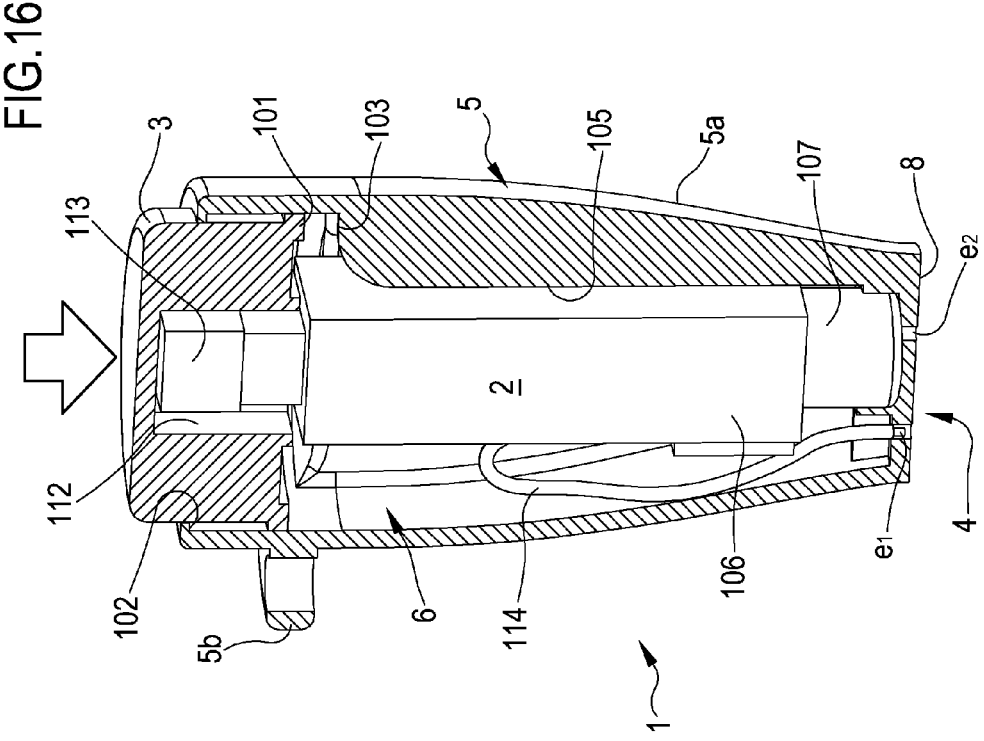
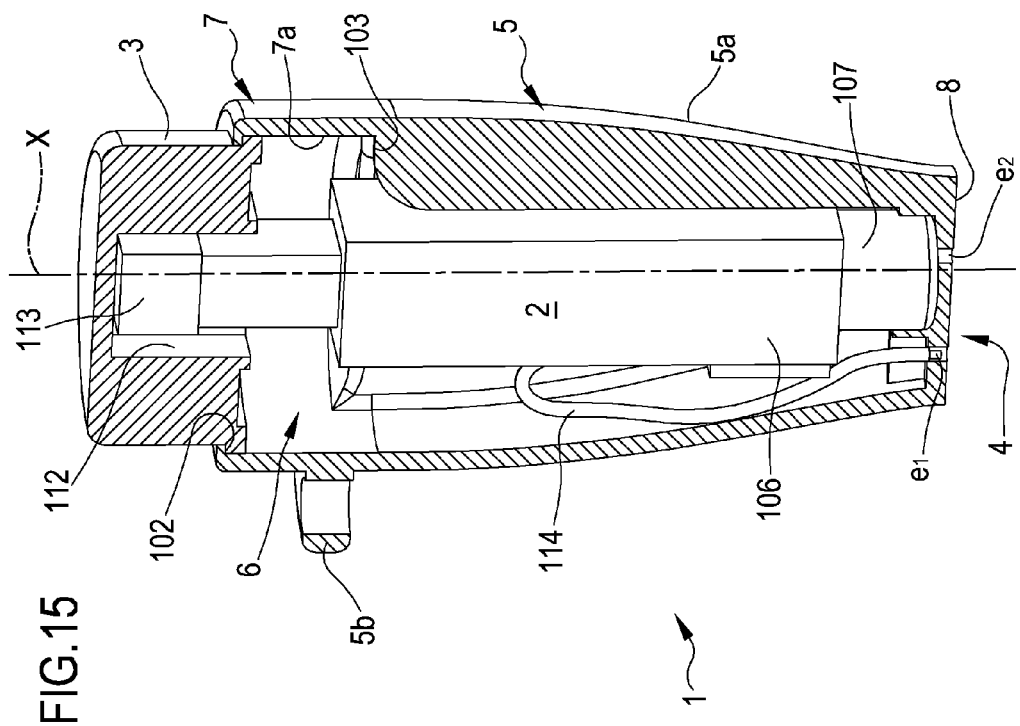

PORTABLE DEVICE FOR TREATING INSECT BITES AND THE LIKE

CROSS-REFERENCE TO RELATED APPLICATIONS

The present application is a Continuation in Part Application of co-pending U.S. application Ser. No. 12/514,521, now issuing as U.S. patent at n. U.S. Pat. No. 8,712,555.

DESCRIPTION

The present invention relates to a portable device for treating the bites or stings of insects and harmful creatures.

BACKGROUND OF THE INVENTION

As it is known, in the event of bites or stings by insects or other creatures which transmit poisons or toxins, it is possible to carry out a local treatment in the area of the bite or sting for the purpose of degrading the poison or toxin which has been injected, by subjecting the tissue to a suitable electrical discharge.

In particular, known treatment devices exploit the piezoelectric effect to generate the electrical discharge: in these devices, the operator (who may be the same person as the victim of the bite or sting), acts on a piezoelectric crystal, usually by means of a direct mechanical control, imposing a "state of stress" on the crystal, which reacts by generating a difference in potential. By connecting the two poles of the crystal to suitable terminals, and positioning these terminals in close proximity to the area of the bite or sting on the victim, it is thus possible to discharge this difference in potential in the area, thus acting on the toxins or poisons injected.

The present applicant has designed a device of this kind, as described and claimed in patent EP0788809: this device has an upper control button, a piezoelectric crystal subject to the upper control button and a discharge area suitably positionable over the area to be treated.

All the components making up the device are contained in a shell of a material which may be electrically conductive or non-conductive, according to the embodiment, and which in the implemented solution is made up of two longitudinal half-shells and two end portions, one of which is shaped in such a way as to be able to house and guide the control button, while the other is positioned close to the discharge zone.

The device, which has been briefly explained, although it is of proven efficacy and has been on the market for some time, has a number of disadvantages in the manufacturing stage.

Indeed, the complex construction of the shell entails a considerable and prolonged working process to assemble it, which has to provide for bringing together and aligning numerous pieces as well as the problematic coupling (for example by gluing or snapping together or ultrasound welding) of the two longitudinal half-shells of the containing body.

The long and onerous assembly process, which moreover entails difficulties of automation and must provide for the insertion and alignment of the piezoelectric element, the discharge area (with the relative terminals) and the control button, increases the labor time and in the last analysis the costs of production.

Furthermore, the fact that two separate half-shells are involved entails the possibility that pieces with slightly different shades of color could be assembled together (as a result for example of different storage conditions or the two half-shells coming from different molding batches), thus resulting in a product of inferior overall quality.

BRIEF SUMMARY OF THE INVENTION

An object of the present invention is to create a portable device for treating the bites or stings of insects and harmful creatures, capable of obviating the disadvantages just presented.

In particular, the present invention proposes to design a device, which can be assembled more easily and quickly, at the same time ensuring the correct positioning of the components capable of generating the treating electrical discharge.

The present invention also has the object of allowing the manufacture of a device with high and repeatable quality standards, avoiding as far as possible any lack of homogeneity in the appearance or exterior shape of the device itself.

Finally, the present invention desires to achieve the goal of reducing production costs and at the same time achieving better ergonomic performance, portability and practicality in use.

BRIEF DESCRIPTION OF THE SEVERAL VIEWS OF THE DRAWING

These and other objects are achieved by a portable device for treating the bites or stings of insects and harmful creatures in accordance with the present invention, having the characteristics set forth in the accompanying claims and illustrated below in several non-limiting embodiments, and also in the attached drawings, in which:

FIG. 9 shows a lower shell of a 'syringe' embodiment;

FIG. 10 is a perspective view of the shell of FIG. 9;

FIG. 11 is a top view of the shell of FIG. 9;

FIG. 12 is an exploded view of the 'syringe' embodiment;

FIGS. 13 and 14 are a partially assembled views of the 'syringe' embodiment;

FIGS. 15 and 16 are section views of the 'syringe' embodiment in an inactivated condition and in an activated condition respectively.

DETAILED DESCRIPTION OF THE INVENTION

Figure 1:
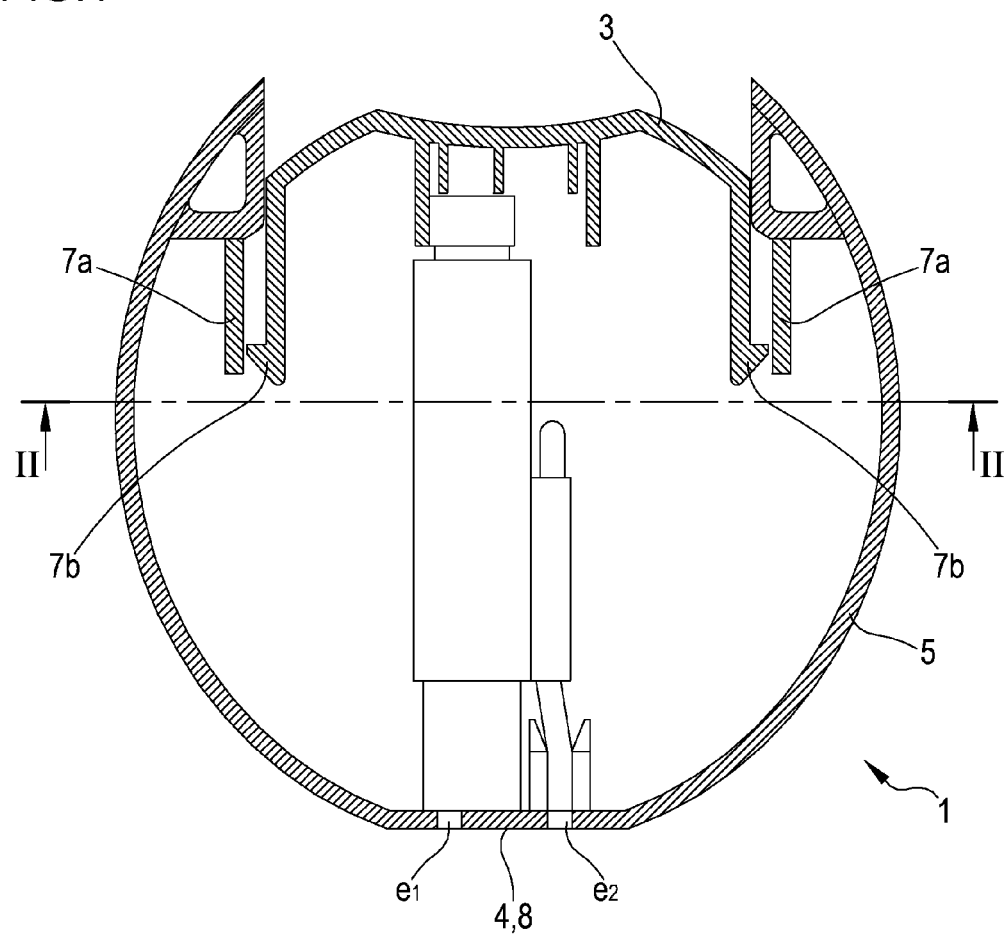
FIG. 1 shows a frontal view in section of a first embodiment of the device.

With reference to the attached drawings, the portable device for treating the bites or stings of insects and harmful creatures according to the invention is generally indicated by the number 1 and substantially comprises a piezoelectric element 2 capable of producing a predetermined difference in electrical potential, an actuating element 3 operable by a user and coupled to the piezoelectric element 2 in order to impart to it at least one predetermined state of stress/deformation and a discharge area 4 electrically connected to the piezoelectric element 2 and positionable in proximity to an area of a patient which has been bitten/stung in order to impart to it an electrical discharge generated by the above-mentioned difference in electrical potential.

Structurally, it should be observed that the piezoelectric element 2 forms two electrical poles (which may otherwise be referred to as ends or electrodes, marked e1 and e2 in the attached drawings), and in the discharge area 4 in turn, two polarized portions are created, which are respectively connected to one of these electrical poles.

Conveniently, the material and the shape of the polarized portions, as well as the modalities of their electrical connection to the poles of the piezoelectric element 2 may be of any kind whatever, provided that they are suitable for making an adequate electrical discharge (of appropriate voltage and amperage) circulate under the skin, in the area of the bite or sting.

Still from a structural point of view, we should note the presence of a containing body 5, which is advantageously monolithic and is capable of housing the piezoelectric element 2, the actuating element 3 and defines the discharge area 4.

In other words, in this embodiment the containing body 5 is made in a single piece and creates an internal housing space 6: this internal housing space is intended to at least partially house the piezoelectric element 2.

In order to ensure the correct inter-operability of the various structural components presented above, the containing body 5 has a guide and housing portion 7 capable of receiving the actuating element 3: in more detail, this guide and housing portion 7 has at least one sliding guide 7a, engageable by the actuating element 3 (which for its part has suitable insertion and guide counterparts 7b, such as for example the teeth illustrated in the attached drawings, which are snapped into place in their respective sliding guides 7a at the time of assembling device 1 and remain stably channeled there during the use of the actuating element by an operator).

The containing element 5 also has an operating portion 8 substantially corresponding to the discharge area 4: in other words, a suitable portion of the external surface of the containing body 5 coincides with the area for pressing on the zone where the bite or sting has been inflicted.

From an ergonomic point of view, it should be observed that the preferred (but not exclusive) embodiment described here has an architecture in which the piezoelectric element 2, the actuating element 3 and the discharge area 4 are mutually aligned along an identical operating axis X: this operating axis X is conveniently the axis of symmetry of the containing body 5. In any event, if the constructional needs of the moment require it, the piezoelectric element 2 can also not be positioned exactly on this axis but slightly displaced or offset with respect to the axis of symmetry of the containing body 5: in particular, the offset arrangement of the piezoelectric element can be implemented in such a way that the two ends or electrodes or poles are centered, equidistantly for example, around the axis of symmetry of body 5.

Still with reference to the attached drawings, it may also be noted that the containing body 5 includes a primary portion 5a forming within itself said housing space 6 and at least one secondary portion 5b adjacent to this primary portion 5a: the conformation and the arrangement of the latter secondary portion 5b can be designed so as to respond to various ergonomic and structural robustness requirements of the device 1.

With reference to the attached drawings 1 to 8, it may for example be seen that the containing body 5 includes two secondary portions 5b arranged symmetrically on opposite sides with respect to the primary portion 5a: in this way it is possible simultaneously to provide a better grip for the user, and at the same time to achieve a high degree of rigidity and structural integrity, all favoring the possibility of exercising the appropriate mechanical pressure on the actuating element without incurring the risk of structural failure of the rest of the device itself. Again in order to endow the device with greater precision and ease of manipulation,—there are also ergonomic interfacing surfaces 9 and/or 11, which are located externally on the primary portions 5a and/or secondary portions 5b and are conveniently capable of improving the grip and/or the manipulation of device 1 on the part of a user.

In order to be able to provide device 1 with carrying straps or similar, there can finally be one or more connecting slots 10, formed in connecting body 5 and located in any position, provided that they are suitable—for being connected to a thread-like or ribbon-like or chain-type element or similar means. A particularly practical example is to connect the product to a key ring by means of a slot 10 to have the product always within reach and ready for use. In a second embodiment of the present invention, the containing body 5 includes a monolithic shell reversibly or irreversibly configurable between an assembly condition in which it allows the insertion of the piezoelectric element 2 and/or the actuating element 3, and an operating condition in which it creates the housing space 6.

As may be seen in the attached drawings 1 to 8, the containing body 5 may be made up of two lobes 5c, respectively counter-profiled, joined without breach of continuity and by mutually opposed parts, to a connecting section 5d.

More particularly, it may be seen that connecting section 5d includes one or more pliable portions 5e (or in other words pre-programmed folding lines) which allow the two lobes 5c to be brought together, thus constituting the operating condition of the containing body 5. Operationally, the closure of the two lobes 5c (and therefore the creation of the housing space 6) is ensured by suitable connection means: for example, it is possible to provide snap and/or mortise closure means 5f, which are operationally activated between the two lobes 5c, preferably after the insertion of the piezoelectric element 2 and/or the actuating element 3.

From the point of view of the assembly procedure, snap closure means do not require ultrasound welding or gluing, and by contrast with a simple mortise closure they ensure that the joint holds together even in the event of a fall (thus avoiding the possibility, in the event that the whole object 1 is accidentally dropped, of small fragments of the internal mechanism being scattered in uncontrolled manner into the environment).

From the point of view of the choice of materials, it is possible to make the containing body 5 and/or the actuating element 3 entirely or partially out of conductive material (for example conductive plastic, or plastic coated with a conductive treatment such as chroming, nickel plating, gold plating or many-others). This means that only one electrode is necessary, because one of the two poles of the device (typically the negative pole) is constituted by the containing body 5 itself, while the electrical circuit which allows the electrical discharge to be sent through the zone to be treated is closed through the hand of the operator/patient grasping the device 1, and more precisely is closed by passing through the arm and body of the user as far as the application point of the apparatus to the area of skin to be treated.

When made of electrically conductive material, the containing body 5 and/or the actuating element 3 function in practice as electrode, so as to allow the passage of an electrical discharge. At all events, in order to avoid "short circuit" problems in the discharge area 4 (i.e. in order to avoid the electrical discharge passing directly from one electrical pole to the other on device 1, without penetrating the patient's skin), electrically insulating means can be provided in proximity to at least one of the two electrodes or electrical poles connected to the piezoelectric element 2 (for example, located around the wire which constitutes the positive pole).

It should be noted that, irrespective of the material of which the various parts of device 1 are made, the two electrodes or electrical poles can either consist of point (or discrete) areas positioned at a certain relative distance on the discharge area, or consist of a combination of a single point or discrete electrode/pole and a given portion of (typically external) surface of the containing body 5 and/or of the actuating element 3: this external surface portion will from time to time be the portion of the device actually in contact with the operator's skin. In any event, it is also possible to make the containing body 5 and/or the actuating element 3 (or more generally, all the parts of the device which come into direct contact with the operator's skin) in electrically insulating material.

In this alternative embodiment it is therefore desirable for the electrical discharge generated by the piezoelectric element 2 to be carried to the tips of the two electrodes located in the discharge area 4.

According to the type and the arrangement of the electrodes (in point or distributed form), the mode of transmitting/propagating the electrical discharge into the patient's body varies: in fact, by using point or discrete electrodes, this electrical discharge will be propagated superficially over the area to be treated (and more particularly within a zone immediately adjacent to the electrodes themselves), while when one of the two poles/electrodes consists of at least one part of the actuating element 3 and/or of the containing body 5, the electrical discharge will travel into the patient's body (passing first through the arm and the hand which has activated the actuating element 3 and/or which holds the device, through the containing body 5 and returning to the device 1 in proximity to the subcutaneous zone corresponding to the area to be treated.

According to this last mode of propagation, the electrical discharge reaches the zone pervaded by the toxin and/or poison with greater efficacy, thus exercising its effects at depth. Still according to this last mode of propagation, it is clear that if the operator of the device 1 does not coincide with the patient, the operator himself/herself must arrange to close the electrical circuit with the patient, for example by touching the latter.

A different embodiment of a portable device for treating the bites or stings of insects and harmful creatures is shown in FIGS. 9-16. This device 1 assumes a syringe-like conformation.

The 'syringe' device includes the monolithic containing body 5 made in a single piece and defining the internal housing space 6; the monolithic containing body 5 is elongated and develops along an operating axis X.

The monolithic containing body 5 is exclusively accessible through an upper opening provided on a guide and housing portion.

The monolithic containing body 5 is geometrically configured so that the piezoelectric element 2 may be inserted from the upper opening in the internal housing space 6 and so that a terminal portion 107 reaches and contacts a flat bottom portion 8 of the monolithic containing body 5.

In other terms, the internal housing space 6 defines a minimum volume configured to let the piezoelectric element 2 to pass through.

The actuating element 3 (operable by a user and associated with said piezoelectric element to impart to the piezoelectric element a predetermined state of stress/deformation), has an enlarged portion 101 to be inserted into the guide and housing portion 7 and sliding along the sliding guide 7a.

As previously described, the actuating element 3, the piezoelectric element 2 and the discharge area 4 are aligned along the operating axis X, meaning that, moving from top to bottom, the actuating element 3, the piezoelectric element 2 and the discharge area are sequentially placed.

The actuating element 3 is movable between an inactive condition substantially emerging from the monolithic containing body 5 (see FIG. 15) and an active condition in which it only partially emerges from the monolithic containing body and in which the piezoelectric element is activated receiving a stress to generate a potential difference (see FIG. 16).

The guide and housing portion 7 comprises an upper abutting portion 102 and a lower abutting portion 103. In the inactive condition, the enlarged portion 101 of the actuating element 3 abuts against the upper abutting portion; in the active condition, the enlarged portion 101 of the actuating element 3 abuts against the lower abutting portion or against the piezoelectric element.

In the shown embodiment, in the active condition, the enlarged portion 101 of the actuating element 3 abuts against a top portion of the main body 106 of the piezoelectric element 2.

In detail, in the movement between the inactive and the active condition, the enlarged portion 101 slides over the sliding guide 7a so that the movement of the actuating element 3 is rectilinear and particularly vertical. The head portion 113 of the piezoelectric element 2 is thereby moved towards the main body 106 and, through an inner mechanism, a mechanical shock is generated against the piezo elements thereby provoking the electric discharge through the electrodes e1, e2.

The head portion 113 is thereafter elastically brought back to the inactive position.

It is to be noted that the monolithic containing body 5 presents a bottom part 104 developing along the operating axis X below the guide and housing portion 7; the bottom part 104 defines the lower part of the internal housing space 6 and has an overall span (orthogonal to the operating axis X) which is constantly smaller than an overall span of the internal housing space 6 defined by the guide and housing portion 7.

In this respect, the bottom part 104 of the monolithic containing body presents a flattened development in a plane orthogonal to the operating axis from top to bottom.

A cross section of the bottom part 104 has a main axis, which is longer that, an auxiliary axis orthogonal to the main axis. The shape of the cross section looks like an oval or an elongated circle.

The bottom part 104 of the monolithic containing body 5 has at least four lateral sides, two longer sides facing one another and two shorter sides facing one another.

Each longer side is connected to two respective shorter sides and each shorter side is connected to two longer sides. Moreover, the bottom part is also tapered towards the flat bottom portion 8.

Differently the guide and housing portion 7 (surmounting the bottom part 104) has a circular cross section and is axial-symmetric.

The connection between the guide and housing portion 7 and the bottom part 104 is obtained through joint portions, in particular by means of two joint portions defining the lower abutting surfaces 103 (see FIGS. 10 and 13).

Moving to the geometry of the internal housing space 6, the bottom part 104 of the monolithic containing body includes a plurality of sliding wings 105 developing along the operating axis X and receiving the piezoelectric element 2.

The sliding wings 105 emerge from the lateral sides of the monolithic containing body towards the internal housing space 6 and have a constant thickness along their extension.

Since the piezoelectric element 2 has a main body 106 of prismatic configuration, the sliding wings contact at least three lateral sides of the main body. FIG. 13 shows the piezoelectric element 2 housed in the internal space 6. The wings 105 contacts the lateral surface of piezo element 2 and keep the element 2 in proper position during working. In detail, two parallel wings are provided on a first and on a second opposite side of the main body 106. A further wing 105 is positioned on a third side opposite to the wire 114.

The sliding wings 105 extend from top to bottom of the bottom part 104 of the monolithic body 5.

The monolithic containing body 5 further includes a flat bottom portion 8 exhibiting at least a first hole 109 and a receiving slot 108 emerging therefrom (see FIG. 11).

The piezoelectric element 2 has a terminal portion 107 placed in correspondence of the bottom portion 8 and of the first hole 109; the terminal portion 107 is received and partially inserted/housed in the receiving slot.

The receiving slot 108 is delimited by a vertical wall and the terminal portion 107 of the piezoelectric element is surrounded by the vertical wall (see FIG. 16). The terminal portion 107 of the piezoelectric element 2 is circular in shape and the receiving slot 108 is circular in shape as well and counter-shaped to the terminal portion 107.

The flat bottom portion 8 of the monolithic body 5 exhibits at least a second hole 110 and ribs 111 emerging therefrom; the piezoelectric element 2 has a wire 114 for connection to the second face of the piezo element.

The wire 114 has the other terminal end placed in correspondence of the bottom portion 8 and particularly in correspondence of the second hole 110; the end is received and partially housed between the ribs.

The ribs 111 emerges vertically from the flat bottom 8 and are at least two, facing each other from respective sides of the end of the wire 114.

The ribs are directly connected to the receiving slot 108 to strengthen the bottom portion of the device.

The containing body comprises a primary portion 5a defining within itself said housing space and at least one secondary portion 5b adjacent to said primary portion.

The secondary portion 5b emerges radially away from the primary portion and develops in a direction substantially orthogonal to the operating axis X. The secondary portion 5b further comprises at least one connecting slot 10 formed in the connecting body.

The containing body and the actuating element are made of electrically non-conductive material so that the electric discharge occurs between the two electrodes e1 and e2 placed in correspondence of the bottom portion 8 of the device where the two holes 109 and 110 are provided.

In a different embodiment, the actuating element may be made at least partially of electrically conductive material, thereby working as an electrode to allow the passage of an electrical discharge.

The activating element 3 has a housing seat 112 and a head portion 113 of the piezoelectric element 2 is housed in the housing seat 112 and moved by moving the activating element 3 from the inactive to the active condition. In particular, the enlarged portion 101 of the actuating element 3 is configured for being inserted by snap-fitting into the respective sliding guide 7a.

Moreover, the monolithic containing body is made by injection molding and is configured to be extracted from the mold according the operating axis X.

Indeed the sliding wings 105 are all directed along the extraction direction and the internal housing space is so configured as to avoid any abutting portion/surface, which could prevent the extraction from the mold of the containing body.

For example, the walls of the receiving slot 108 and of the ribs 111 are vertical and directed along the extraction direction; the sole remaining abutting surface defined along the extraction direction is the upper abutting surface 102 which has however a prefixed dimension so that it may be elastically deformed without impairing the integrity of the monolithic body 5, thereby allowing proper extraction from the mold.

From the assembling point of view, a new method of assembling a portable device for treating the bites or stings of insects and harmful creatures is hereinafter described.

The method includes the following steps:
defining in a mold a monolithic containing body made in a single piece by injection molding; the containing body is made in s single piece of plastic material;
extracting the monolithic containing body from the mold along the operating axis, in particular the containing body being made of a material at least in part elastic. The upper abutting portion being elastically deformed so that the body is extracted from the mold;
providing the piezoelectric element as above described;
providing the actuating element as above described;
introducing the piezoelectric element in the internal housing space along a direction substantially coinciding with the operating axis so that a terminal portion of the piezoelectric element abuts against a flat bottom of the monolithic containing body; the sliding wings guiding the insertion and keeping the piezo element in the right angular position so that the end of the wire is in place once the piezo element is inserted;
introducing the enlarged portion of the actuating element into the guide and housing portion of the monolithic containing body; this step again taking advantage of the partial elasticity of the top portion of the monolithic body.

Figure 2:
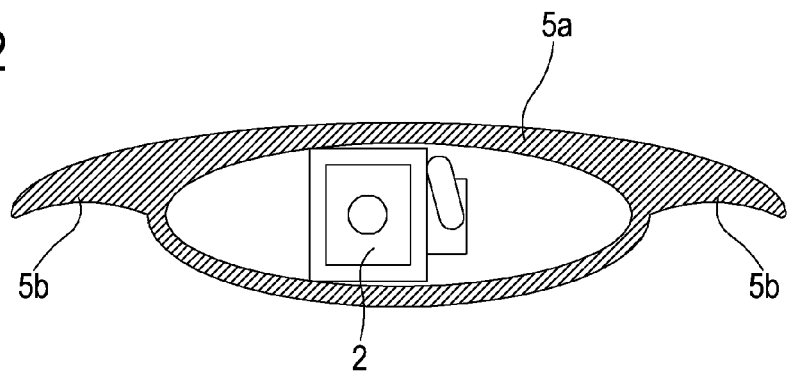
FIG. 2 shows a top view in section along the line II-II of the device shown in FIG. 1.
Figure 3:
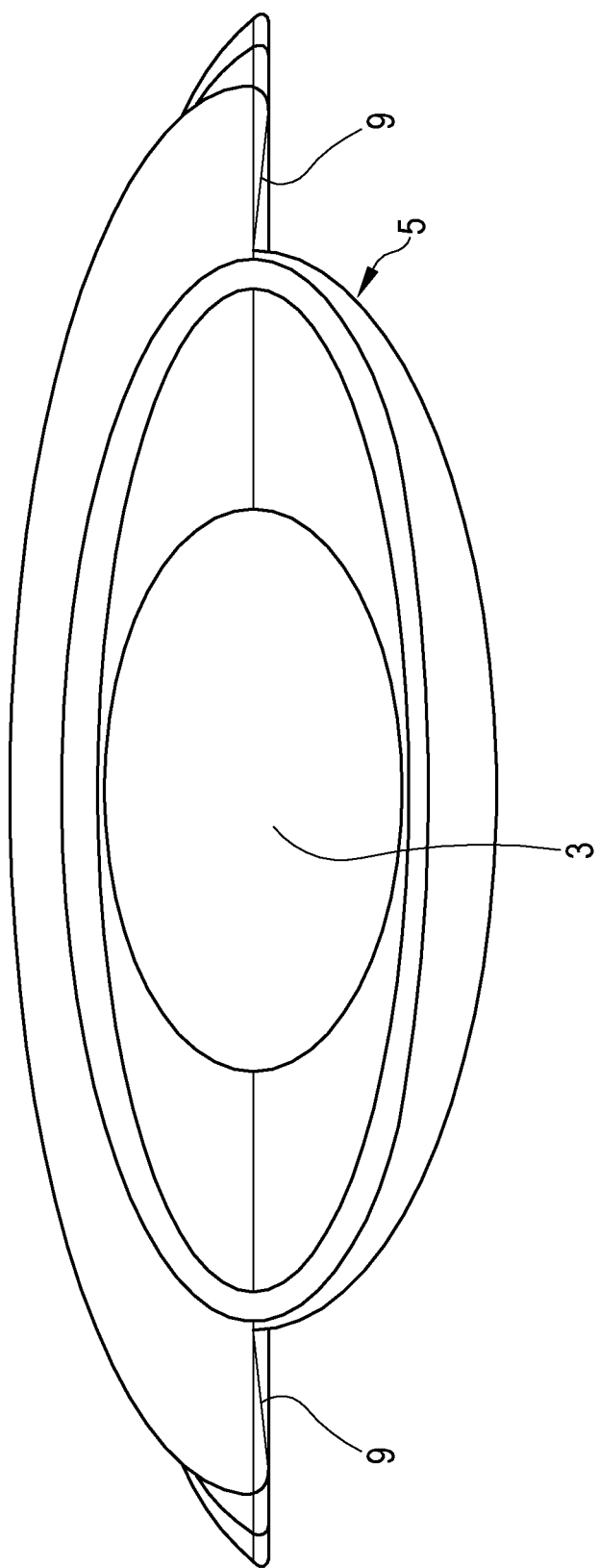
FIGS. 3, 4a and 4b show top views of several variant embodiments of the device.
Figure 5A:
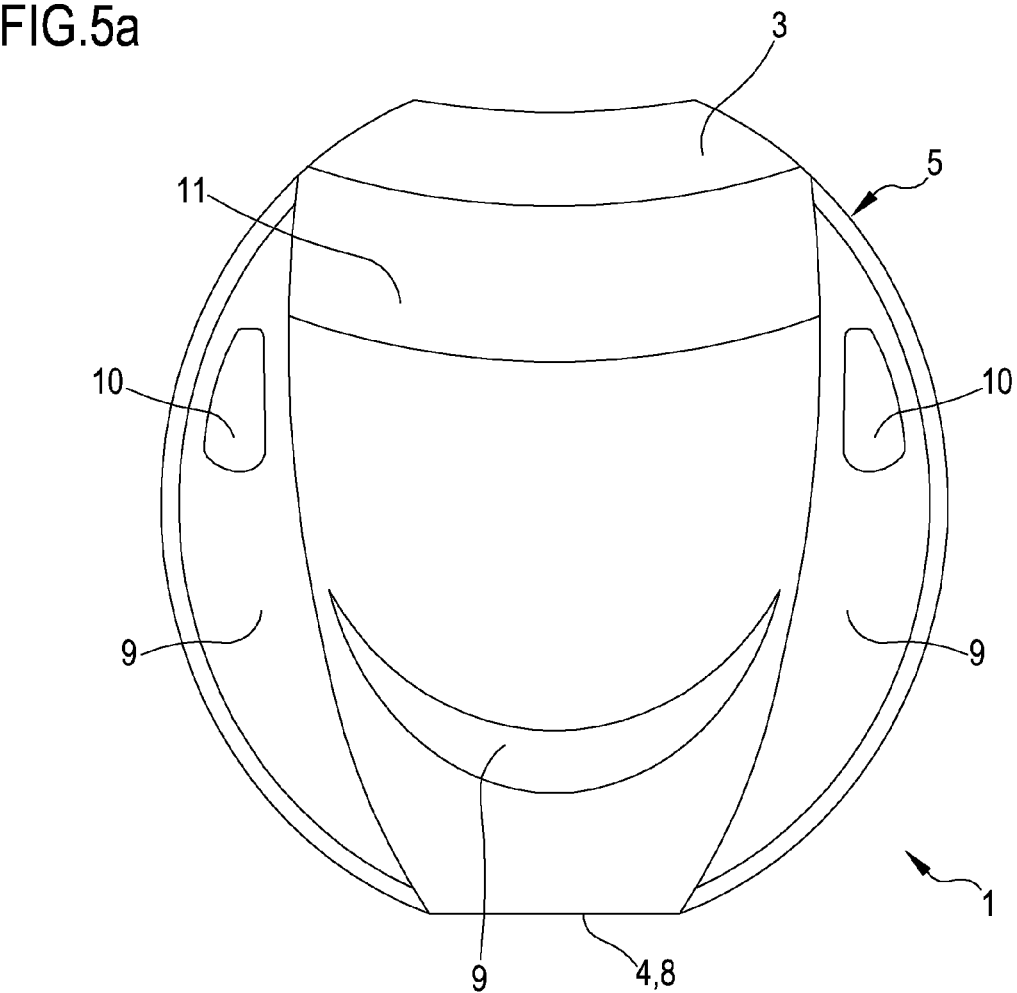
FIGS. 5a and 5b show front views of several variant embodiments of the device.
Figure 4A:
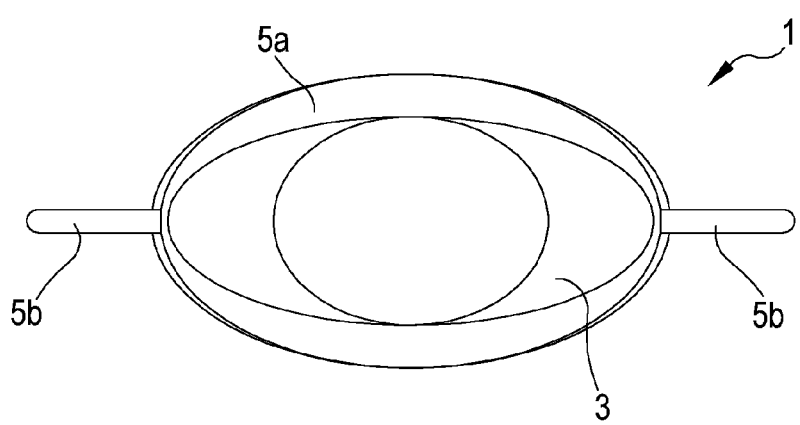
Figure 4B:
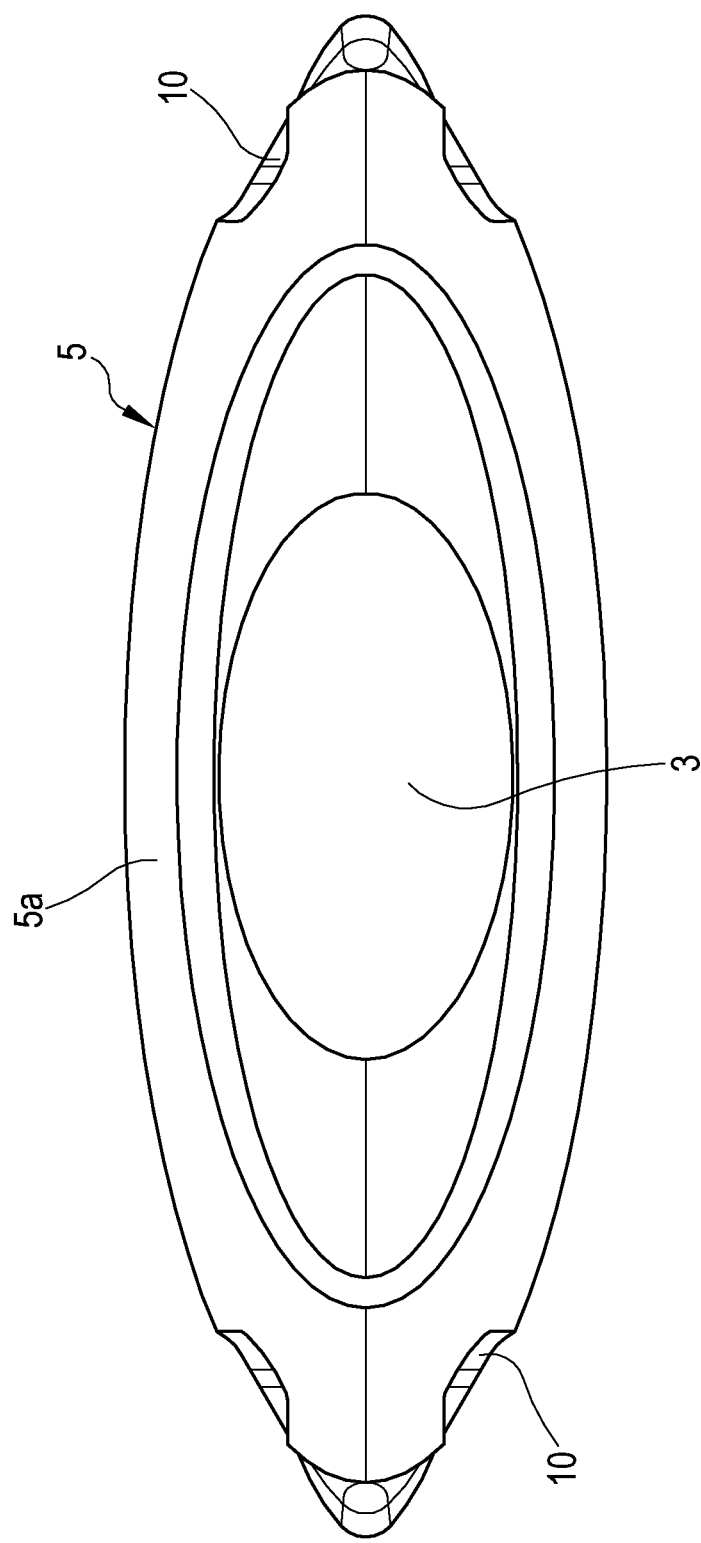
Figure 5B:
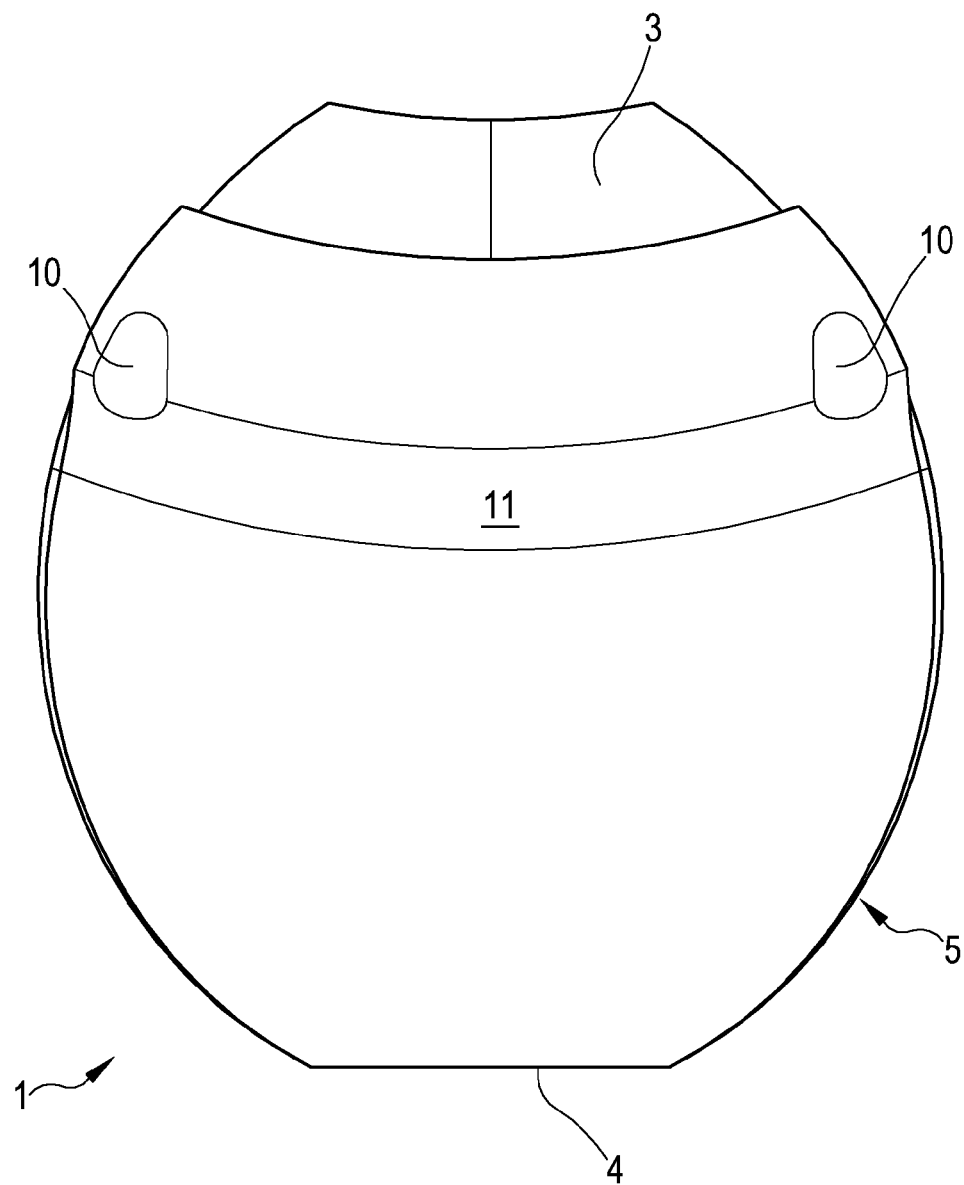
Figure 6:
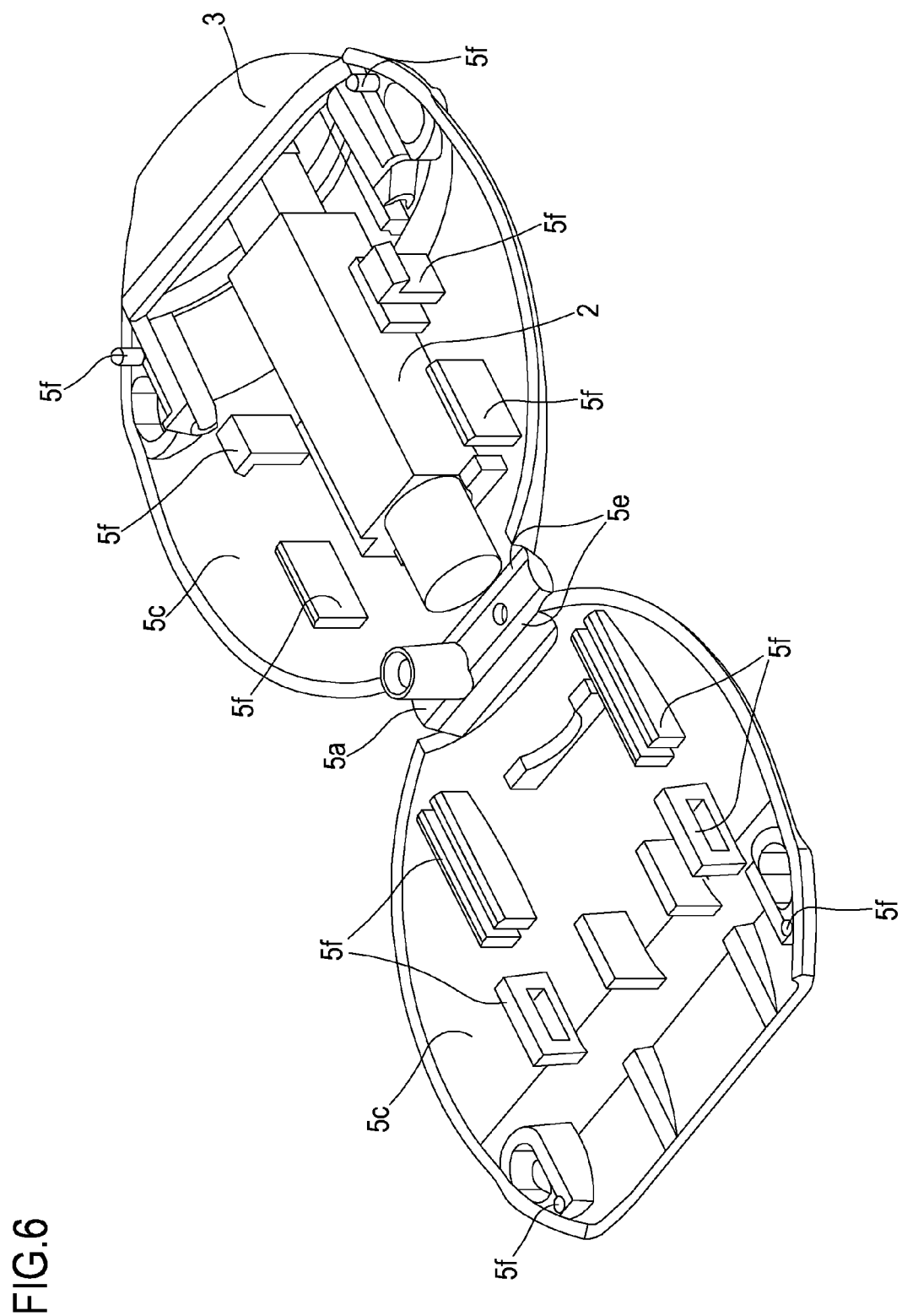
FIG. 6 shows a perspective view of a second embodiment of the device in a half-assembled configuration.
Figure 7:
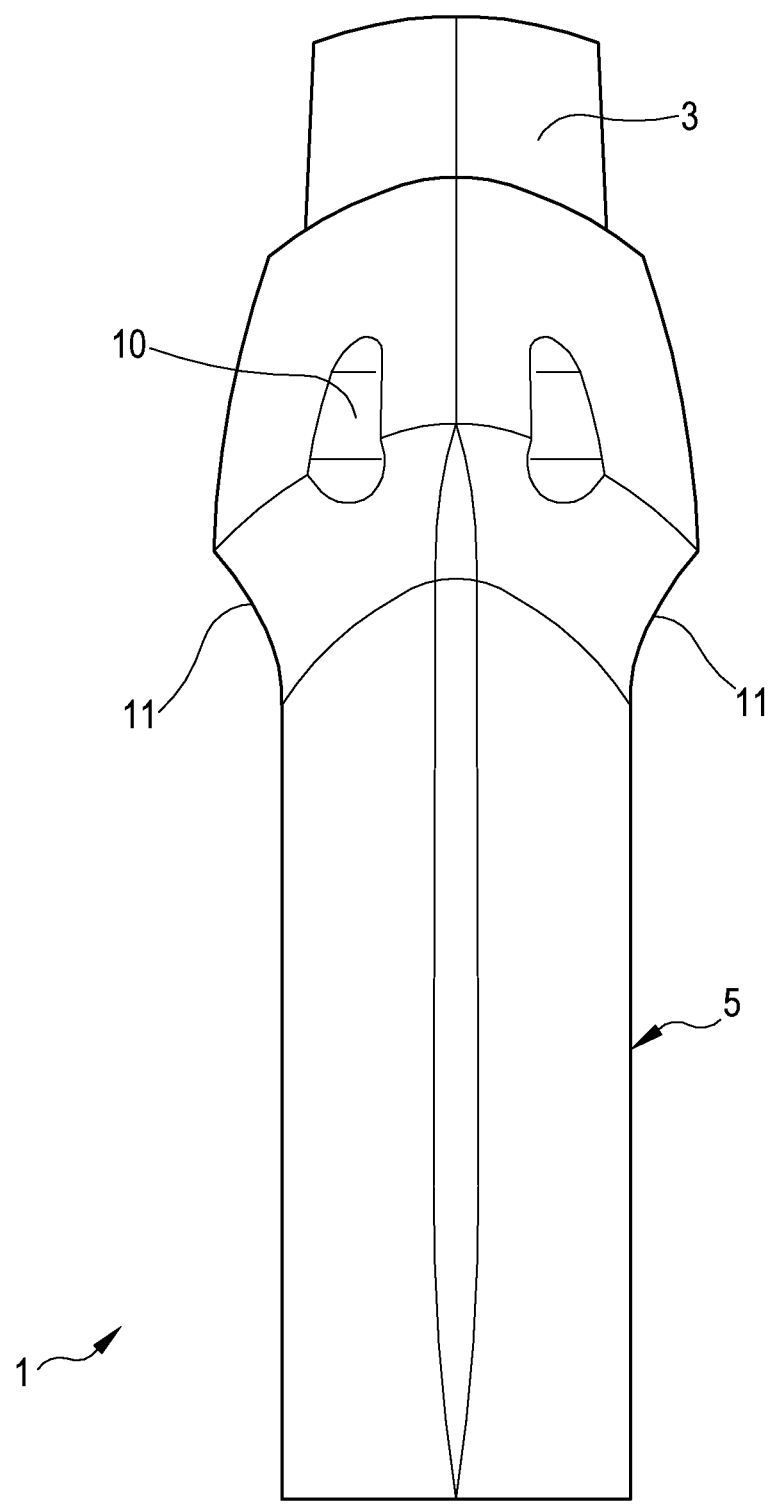
FIG. 7 shows a lateral view of the device shown in FIG. 6.
Figure 8:
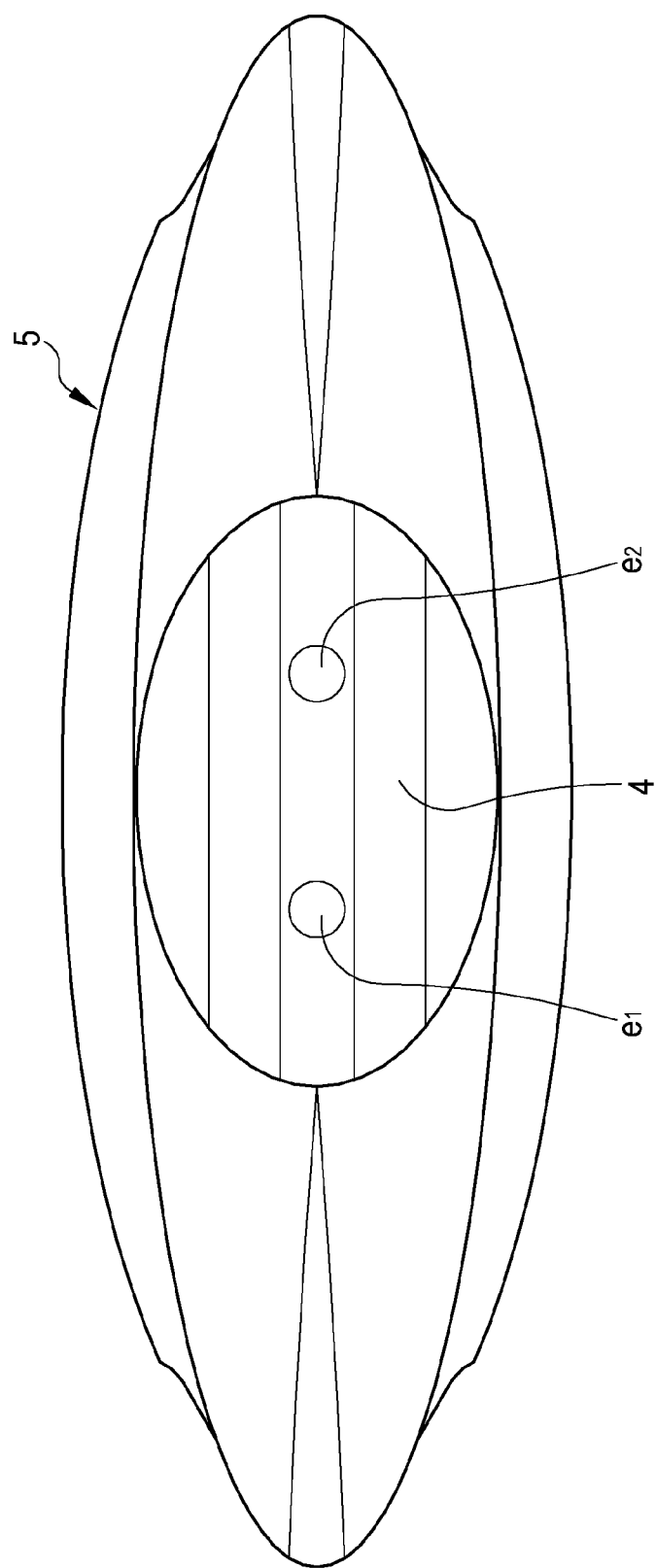
FIG. 8 shows a bottom view of a device.

In accordance with the present invention it is advantageously possible to implement a further new and original assembly method for the embodiment of FIGS. 1 to 8: this method requires first of all the provision of a monolithic shell (which conveniently includes two lobes and a connecting section and which will be configurable as above), of a piezoelectric element and an actuating element, and secondly requires the positioning of these last pieces inside a housing space created by the containing body itself. In particular, the present method requires that the step of the creation of the above-mentioned containing space should take place by bringing the two lobes together at least in proximity to the actual connecting section, which joins them.

According to the needs of the moment, the creation of the containing space can take place before, simultaneously with or after the positioning of the actuating element and the piezoelectric element. The method just explained is implementable on the second variant embodiment of the device according to the present invention: in any case, the step of the creation of the housing space can even be activated, in the first embodiment of the device, for example by the injection-moulding of a monolithic shell or similar process.

The invention enables important advantages to be achieved. First of all, it should be noted that the peculiar constructional architecture of the containing shell enables the achievement of a significant reduction in production times, accompanied by an equally significant reduction in the complexity of the assembly operation: indeed, thanks to the "one-piece" conformation of the shell and the appropriate provision of the housing space, the positioning and alignment of the piezoelectric element and the other sub-components associated with it are extremely quick and precise, and can actually be performed by a single operator (or indeed be automated).

In other words, the present invention achieves a considerable improvement in the production process, avoiding involvement in complex and delicate operations of coupling several parts of the containing shell.

Secondly, it should be noted that the provision of the monolithic shell enables problems of poor quality in the alignment and assembly of two or more half-shells to be avoided, and at the same time avoids the manufacture of finished products in which the different parts of the shell are of different shades of color.

Finally, the present invention allows the creation of a portable device for treating the bites or stings of insects and harmful creatures with low costs of production and sale, and at the same time makes the object itself easier for the end user to manipulate and carry.

The invention claimed is:

1. A portable device for treating the bites or stings of insects and harmful creatures, comprising:
   a monolithic containing body made in a single piece and defining an internal housing space, the monolithic containing body develops along an operating axis and has a guide and housing portion with a sliding guide;
   a piezoelectric element configured for producing a predetermined difference in electrical potential, the piezoelectric element being housed in the internal housing space of the monolithic containing body;
   an actuating element operable by a user and associated with said piezoelectric element to impart to the piezoelectric element a predetermined state of stress/deformation, the actuating element having an enlarged portion inserted in the guide and housing portion and sliding along the sliding guide;
   a discharge area electrically connected to the piezoelectric element and positionable close to an area of a patient which has been bitten/stung in order to impart to the area an electrical discharge generated by said difference in electrical potential;
   wherein the actuating element, the piezoelectric element and the discharge area are aligned along the operating axis, the actuating element being movable between an inactive condition substantially emerging from the monolithic containing body and an active condition only partially emerging from the monolithic containing body in which the piezoelectric element is activated receiving a stress to generate a potential difference, and
   wherein the guide and housing portion comprises an upper abutting portion and a lower abutting portion, in the inactive condition, the enlarged portion of the actuating element abutting against the upper abutting portion, in the active condition, the enlarged portion of the actuating element abutting against the lower abutting portion or against the piezoelectric element,
   the monolithic containing body presenting a bottom part developing along the operating axis below the guide and housing portion, the bottom part defining part of the internal housing space with an overall span orthogonal to the operating axis which is constantly smaller than an overall span of the internal housing space defined by the guide and housing portion.

2. A device according to claim 1, wherein the bottom part of the monolithic containing body includes a plurality of sliding wings developing along the operating axis, said sliding wings receiving the piezoelectric element.

3. A device according to claim 2, wherein the piezoelectric element has a main body of prismatic configuration, the sliding wings contacting at least three lateral sides of the main body.

4. A device according to claim 2, wherein the sliding wings have a constant thickness along their extension.

5. A device according to claim 1, wherein the enlarged portion of the actuating element is configured for being inserted by snap-fit into the respective sliding guide.

6. A device according to claim 1, wherein the piezoelectric element, the actuating element and the discharge area are mutually aligned along the same operating axis, said operating axis being an axis of symmetry of the containing body.

7. A device according to claim 1, wherein the containing body comprises a primary portion defining within itself said housing space and at least one secondary portion adjacent to said primary portion, the secondary portion emerging radially away from the primary portion, the secondary portion developing in a direction substantially orthogonal to the operating axis.

8. A device according to claim 1, further comprising at least one connecting slot formed in the connecting body.

9. A device according to claim 1, wherein the containing body and the actuating element are made of electrically non-conductive material.

10. A device according to claim 1, wherein the actuating element is made at least partially of electrically conductive material, the actuating element working as an electrode to allow the passage of an electrical discharge.

11. A device according to claim 1, wherein the monolithic containing body includes a flat bottom portion exhibiting at least a first hole and a receiving slot emerging therefrom, the piezoelectric element having a terminal portion placed in correspondence of the bottom portion and of the first hole, the terminal portion being received and partially housed in the receiving slot.

12. A device according to claim 11, wherein the receiving slot is delimited by a vertical wall, the terminal portion of the piezoelectric element being surrounded by the vertical wall, the terminal portion of the piezoelectric element being circular in shape, the receiving slot being circular in shape.

13. A device according to claim 1, wherein the monolithic containing body includes a flat bottom portion exhibiting at least a second hole and ribs emerging therefrom, the piezoelectric element having a wire having an end placed in correspondence of the bottom portion and of the second hole, the end being received and partially housed between the ribs.

14. A device according to claim 13, wherein the ribs emerges vertically from the flat bottom and are at least two facing from respective sides of the end of the wire.

15. A device according to claim 1, wherein the monolithic containing body is made by injection molding and is configured to be extracted from the mold according the operating axis.

16. A device according to claim 1, wherein the activating element has a housing seat, a head portion of the piezoelectric element being housed in the housing seat and moved by moving the activating element from the inactive to the active condition.

17. A device according to claim 1, wherein the bottom part of the monolithic containing body presents a flattened development, in a plane orthogonal to the operating axis, a section of the bottom part having a main axis which is longer that an auxiliary axis orthogonal to the main axis.

18. A device according to claim 1, wherein the bottom part of the monolithic containing body has at least four lateral sides, two longer sides facing one another, two shorter sides facing one another, a longer side being connected to two respective shorter sides, a shorter side being connected to two longer sides.

19. A device according to claim 1, wherein the guide and housing portion has a circular cross section and is axial-symmetric.

20. A method of assembling a portable device for treating the bites or stings of insects and harmful creatures, the portable device comprising:
 a monolithic containing body made in a single piece and defining an internal housing space, the monolithic containing body develops along an operating axis and has a guide and housing portion with a sliding guide;
 a piezoelectric element configured for producing a predetermined difference in electrical potential, the piezoelectric element being housed in the internal housing space of the monolithic containing body;
 an actuating element operable by a user and associated with said piezoelectric element to impart to the piezoelectric element a predetermined state of stress/deformation, the actuating element having an enlarged portion inserted in the guide and housing portion and sliding along the sliding guide;
 a discharge area electrically connected to the piezoelectric element and positionable close to an area of a patient which has been bitten/stung in order to impart to the area an electrical discharge generated by said difference in electrical potential;
 wherein the actuating element, the piezoelectric element and the discharge area are aligned along the operating axis, the actuating element being movable between an inactive condition substantially emerging from the monolithic containing body and an active condition only partially emerging from the monolithic containing body in which the piezoelectric element is activated receiving a stress to generate a potential difference, and
 wherein the guide and housing portion comprises an upper abutting portion and a lower abutting portion, in the inactive condition, the enlarged portion of the actuating element abutting against the upper abutting portion, in the active condition, the enlarged portion of the actuating element abutting against the lower abutting portion or against the piezoelectric element,
 the monolithic containing body presenting a bottom part developing along the operating axis below the guide and housing portion, the bottom part defining part of the internal housing space with an overall span orthogonal to the operating axis which is constantly smaller than an overall span of the internal housing space defined by the guide and housing portion.
 the method includes the following steps:
  defining in a mold a monolithic containing body made in a single piece by injection molding;
  extracting the monolithic containing body from the mold along the operating axis;
  providing the piezoelectric element;
  providing the actuating element;
  introducing the piezoelectric element in the internal housing space along a direction substantially coinciding with the operating axis so that a terminal portion of the piezoelectric element abuts against a flat bottom of the monolithic containing body;
  introducing the enlarged portion of the actuating element into the guide and housing portion of the monolithic containing body.

* * * * *